United States Patent [19]

Shima et al.

[11] Patent Number: 5,225,594
[45] Date of Patent: Jul. 6, 1993

[54] PROCESS FOR PRODUCING METHACRYLIC ACID

[75] Inventors: Yoshikazu Shima; Takafumi Abe; Hirofumi Higuchi, all of Niigata, Japan

[73] Assignee: Mitsubishi Gas Chemical Company, Inc., Tokyo, Japan

[21] Appl. No.: 759,468

[22] Filed: Sep. 13, 1991

[30] Foreign Application Priority Data

Nov. 28, 1990 [JP] Japan .................. 2-322464

[51] Int. Cl.$^5$ .................. C07B 35/00; C07C 51/00
[52] U.S. Cl. .................................. 562/599
[58] Field of Search ........................... 562/599

[56] References Cited

U.S. PATENT DOCUMENTS 5,087,737  2/1992  Higuchi et al. .................. 560/215

OTHER PUBLICATIONS

Morrison & Boyd 5th Ed p. 875.

Primary Examiner—Paul J. Killos
Assistant Examiner—Jospeh M. Conrad
Attorney, Agent, or Firm—Frishauf, Holtz, Goodman & Woodward

[57] ABSTRACT

A process for producing methacrylic acid which comprises: (I) producing acetonecyanohydrin from prussic acid and acetone; (II) hydrating the acetonecyanohydrin obtained in step (I) to form α-hydroxyisobutyric acid amide; (III) reacting the α-hydroxyisobutyric acid amide obtained in step (II) with methyl formate or with methanol and carbon monoxide to form methyl α-hydroxyisobutyrate and formamide; (IV) hydrolyzing the methyl α-hydroxyisobutyrate obtained in step (III) to form α-hydroxyisobutyric acid; (V) dehydrating the α-hydroxyisobutyric acid obtained in step (IV) to form methacrylic acid; and (VI) dehydrating the formamide separated from the products obtained in step (III) to form prussic acid and recycling the prussic acid to step (I) as a starting material. The process is capable of producing methacrylic acid from readily available starting materials with a high yield and selectivity, without forming undesirable by-product or waste materials, such as ammonium sulfate.

21 Claims, No Drawings

PROCESS FOR PRODUCING METHACRYLIC ACID

BACKGROUND OF THE INVENTION

1. Field of the Invention

The present invention relates to a novel process for producing methacrylic acid from acetone and methyl formate, or from acetone, methanol and carbon monoxide as starting materials.

Methacrylic acid is an extremely important intermediate in industrial use since it is employed in great quantities as a starting material not only for the synthesis of methyl methacrylate but also for the production of various higher esters.

2. Description of the Related Arts

As the process for industrially producing methacrylic acid, (1) the acetonecyanohydrin process in which prussic acid and acetone are used as starting materials and methacrylic acid is produced through acetonecyanohydrin (hereinafter referred to as "ACH") formed from the abovementioned starting materials, and (2) the $C_4$ oxidation process in which isobutylene or tert-butanol is used as a starting material have been put into practical application.

Although there have been proposed a number of processes for producing methacrylic acid in addition to the aforementioned processes such as oxidation-dehydrogenation of isobutyric acid, condensation-dehydration of propionic acid or propionaldehyde and formaldehyde, etc., none of them has yet been put into practice.

The ACH process is a process in which ACH is synthesized from prussic acid and acetone, and then the resultant ACH is reacted with water in the presence of sulfuric acid to produce methacrylic acid.

The ACH process has been widely carried out by virtue of its easy reaction and high yields, but suffers the disadvantage that large amounts of waste sulfuric acid and ammonium sulfate are by-produced and the treatment thereof increases the production cost of methacrylic acid.

On the other hand, the above-mentioned $C_4$ oxidation process suffers from the defects that a number of side reactions take place lowering the yield of methacrylic acid, purification costs are high, a complicated and expensive production plant is required, and the supply of isobutylene or tert-butanol to be used as the starting material is limited.

An intensive research made by the present inventors on the process capable of producing methacrylic acid at an inexpensive cost with easy and stable supply of starting materials finally led to success in accomplishing the present invention.

SUMMARY OF THE INVENTION

It is an object of the present invention to provide a novel process for producing methacrylic acid from starting materials that are easily and stably procured.

It is another object of the present invention to provide a process for producing methacrylic acid with simple operations at a low cost and a high yield without requiring a complicated or expensive production plant.

It is still another object of the present invention to provide a process for producing methacrylic acid without troublesome treatment of by-products or waste materials.

Other objects and advantages of the present invention will become apparent from the detailed description to follow taken in conjunction with the appended claims.

The present invention relates to a process for producing methacrylic acid which comprises:

(I) a step of reacting prussic acid with acetone to form ACH;

(II) a step of hydrating ACH obtained in the preceding step (I) to form α-hydroxyisobutyric acid amide;

(III) a step of reacting α-hydroxyisobutyric acid amide obtained in the preceding step (II) with methyl formate or with methanol and carbon monoxide to form methyl α-hydroxyisobutyrate and formamide;

(IV) a step of hydrolyzing methyl α-hydroxyisobutyrate obtained in the preceding step (III) to form α-hydroxyisobutyric acid;

(V) a step of dehydrating α-hydroxyisobutyric acid obtained in the preceding step (IV) to form methacrylic acid; and (VI) a step of dehydrating formamide separated from the products obtained in the above step (III) to form prussic acid and of recycling the prussic acid to reuse as a starting material.

DESCRIPTION OF PREFERRED EMBODIMENT

The process of the present invention eventually employs acetone and methyl formate, or acetone, methanol and carbon monoxide as starting materials, and produces the objective methacrylic acid through ACH. The process is characterized in that it is not accompanied at all by by-production of ammonium sulfate unlike the conventional ACH process.

Acetone is produced in great quantities at a low cost and further, if necessary, can easily be produced from propylene.

On the other hand, methyl formate can easily be produced by carbonylation or dehydrogenation of methanol which is produced in extremely large quantities at a low cost.

In the process according to the present invention, ACH is produced by reacting prussic acid and acetone by the conventional process. More specifically, ACH can be produced in a high yield by mixing prussic acid and acetone at a temperature as low as about 10° C. in the presence of a basic catalyst such as alkalis or amines.

In the process according to the present invention, α-hydroxyisobutyric acid amide is produced by catalytically reacting a mixture of ACH and water in the presence of a catalyst. As such a catalyst, that which is effective for the hydration reaction of nitriles can be used. Though a strong acid such as sulfuric acid can be used, a metallic or metallic oxide catalyst or the like is desirable from an economical point of view including post-treatment thereof. More specifically, manganese, copper, nickel and oxides thereof are effective. Among them manganese oxide is particularly desirable.

The suitable feed ratio by weight of ACH to water is in the range of 10:90 to 90:10. In the reaction system, a solvent such as acetone or methanol can also be present.

In the case where manganese oxide is used as a catalyst, the reaction temperature is desirably 20° to 150° C., more desirably 40° to 100° C. The reaction time is desirably 0.3 to 6 hours, more desirably 0.5 to 3 hours. The reaction can be carried out batchwise or continuously.

Though the production of methyl α-hydroxyisobutyrate and formamide by the reaction of α-hydroxyisobutyric acid amide and methyl formate, or α-hydroxyisobutyric acid amide, methanol and carbon monoxide can be carried out by heating the mixture of α-hydroxyisobutyric acid amide and methyl formate in the absence of a catalyst, it is more effective to effect the reaction in the presence of a catalyst and a solvent. As the reaction proceeds under an equilibrium condition, the yield of methyl α-hydroxyisobutyrate depends upon the molar feed ratio of methyl formate or methanol and carbon monoxide to α-hydroxyisobutyric acid amide, which ranges desirably from 1/1 to 10/1, more desirably from 2/1 to 5/1. The molar feed ratio of methanol to α-hydroxyisobutyric acid amide ranges from 1/1 to 30/1, desirably from 3/1 to 20/1. The partial pressure of carbon monoxide ranges from 10 to 500 kg/cm$^2$, desirably from 20 to 300 kg/cm$^2$. In the reaction of α-hydroxyisobutyric acid and methylformate, the addition of a solvent is effective in increasing the solubility of α-hydroxyisobutyric acid amide and the selectivity of the reaction. As the solvent to be used, methanol is most desirable, and the molar feed ratio of methanol to α-hydroxyisobutyric acid amide is desirably 2 to 10.

Known catalysts to be used in the above reaction include inorganic acids, organic acids, alkalis and salts thereof as disclosed in Japanese Patent Application Laid-Open Nos. 55444/1983 and 78937/1985.

However, in the case of known catalysts, both the rate of reaction and selectivity are insufficiently low. Continuous research and development on a high-performance catalyst by the present inventors resulted in the finding that alkali metal alcoholate and alkaline earth metal oxide were extremely excellent as a catalyst for use in the aforementioned reaction as disclosed in Japanese Patent Application Laid-Open No. 290650/1989.

The alkali metal alcoholate is synthesized from metallic lithium, sodium or potassium and a lower alcohol.

Examples of the alkali metal alcoholate to be used as a catalyst in the above-mentioned reaction include methylate, ethylate and butyrate of sodium or potassium.

The alkaline earth metal oxide to be used as a catalyst in the above-mentioned reaction is exemplified by magnesium oxide, calcium oxide, barium oxide, etc.

With regard to reaction conditions, when an alkali metal alcoholate or alkaline earth metal oxide is used as a catalyst in the present reaction, the suitable amount of the catalyst to be used is 0.001 to 0.30 per mol of α-hydroxyisobutyric acid amide under the reaction temperature of from 20° to 100° C. and the reaction time of from 0.5 to 6 hours.

The use of an alkali metal alcoholate catalyst in the production of a carboxylic acid ester by alcoholysis of a carboxylic acid amide with alcohol is disclosed in Japanese Patent Application Laid-Open No. 3015/1977.

The alcoholysis, however, suffers the disadvantages that the yield of carboxylic acid ester is low in addition to various problems of processing operation in that the reaction temperature is as high as 200° C. necessitating a high-pressure reactor, and that intermittent release of the pressure in the reaction system is required since ammonia is formed during the reaction.

On the other hand, in the process according to the present invention, when an esterification reaction by the use of methyl formate is applied, all of the disadvantages of the above prior arts can be dissolved.

The reaction product in the process of the present invention is separated and recovered by distillation and the like, and the unreacted materials are recycled to the reaction system as starting materials.

In the process according to the present invention, the production of α-hydroxyisobutyric acid is effected by hydrolyzing methyl α-hydroxyisobutyrate in the presence of an organosulfonic acid catalyst.

Examples of the organosulfonic acid catalyst to be used in the above reaction include organosulfonic acid such as methanesulfonic acid and p-toluenesulfonic acid, and organosulfonic acid with a high molecular weight such as strongly acidic ion exchange resin. Among them, the particularly desirable catalyst judged from the viewpoint of separability of the catalyst from the product is a strongly acidic ion exchange resin, which is capable of producing high-quality α-hydroxyisobutyric acid at a high selectivity and a high yield.

The reaction conditions in the process of the present reaction are selected in accordance with the types of methyl α-hydroxyisobutyrate and the catalyst, but include a temperature in the range of 20° to 150° C., preferably 50° to 120° C. and a reaction time in the range of 5 minutes to 24 hours, preferably 10 minutes to 8 hours.

In the process according to the present invention, the molar ratio of water to methyl α-hydroxyisobutyrate is suitably 1 to 100, but preferably 1 to 10, taking into consideration the cost of energy needed for separation from each other after the reaction.

Any operation and procedure in the process of the present invention can be carried out provided that the catalyst is in contact with the starting material. As the hydrolysis reaction belongs to an equilibrium reaction, however, for the purpose of enhancing the degree of conversion, it is effective to distil away the by-produced methanol to outside the reaction system by a method such as reactive distillation.

In the production of methacrylic acid from α-hydroxyiosbutyric acid by means of dehydration reaction, various known processes are available, in which there can be used catalysts including oxides, hydroxides, halogenides, carbonates, alcoholate, phsophates and organic acid salts of alkali metal or alkaline earth metal, amines, phosphines, ion exchange resins, zeolite, alumina, silica, halogenated quaternary ammonium compounds, etc. Among them is particularly desirable a hydroxide of an alkali metal, which is capable of producing methacrylic acid at a high yield under a relatively mild reaction condition, that is, under a reaction temperature of 160° to 250° C. in accordance with the method disclosed in Japanese Patent Publication No. 45659/1988.

The formamide which is by-produced simultaneously with methyl α-hydroxyisobutyrate is subjected to dehydration reaction to produce prussic acid. The production of prussic acid from formamide according to the present invention is carried out by a known process, in which prussic acid is produced at a high yield by pyrolyzing at 350° to 600° C. under 10 torr to normal pressure in the presence or absence of catalyst. The prussic acid obtained in the above process is separated, recovered, and recycled through the ACH production process for reuse thereof.

According to the process of the present invention, the reaction proceeds with extremely high selectivity at each step, enabling the objective methacrylic acid to be produced at a high yield from acetone and methyl formate, or from acetone, methanol and carbon monoxide. Furthermore, undesirable by-products such as ammonium sulfate produced in the conventional processes are not formed at all, and thus the process of the present invention is of great industrial value.

The present invention will be described in more detail with reference to the following examples, which are not intended to limit the invention thereto.

EXAMPLE 1

Step (I): Synthesis of ACH from Prussic Acid and Acetone 1.16 kg of acetone and 10 ml of 1N aqueous sodium hydroxide solution were placed in a 5-liter flask equipped with a stirrer, a thermometer and a dropping funnel for prussic acid, and 594 g of prussic acid was dropped thereto while maintaining the temperature in the flask at 20° C. After the dropping of prussic acid was finished, the reaction was completed by maintaining the resulting mixture in the flask at 0° to 10° C. for 3 hours. Subsequently, a small amount of 50% sulfuric acid was added thereto to adjust the reaction solution to pH 3.

The flask was connected to a vacuum system, and unreacted prussic acid and acetone were distilled away to outside the reaction system. Thereafter, the content in the flask was subjected to simple distillation at 10 torr to afford 1.67 kg of purified ACH.

The ACH thus obtained had a purity of 99% or higher with a yield of 98.3% based on acetone.

Step (II): Synthesis of $\alpha$-hydroxyisobutyric Acid Amide by Hydration of ACH 50 g of 20 to 32 mesh manganese dioxide catalyst ($\delta$-$MnO_2$ prepared according to P. W. Selwood et al. J. Am. Chem. Soc., 71,3039 (1949)) was packed in a jacketed tubular reactor made of Pyrex glass with an inner diameter of 18 mm and a length of 40 cm while maintaining the temperature in the reactor at 60° C. The starting solution was prepared as a composition consisting of 30% by weight of ACH obtained in the above step (I), 10% by weight of acetone as a guaranteed reagent and 60% by weight of deionized water by ion exchange and subsequently was fed to the reactor at a rate of 33 g/hr by the use of a fixed delivery pump.

The reaction continued for one week to produce 5.5 kg of reaction solution. The result of gas chromatographic analysis of the reaction solution showed that the conversion of ACH was 97.8%, the yield of $\alpha$-hydroxyisobutyric acid amide was 96.1% and small amounts of acetone and formamide were contained therein.

The above reaction solution was distilled under reduced pressure to afford 1.82 kg of $\alpha$-hydroxyisobutyric acid amid having a purity of 99% or higher.

Step (III): Synthesis of Methyl $\alpha$-hydroxyisobutyrate and Formamide from $\alpha$-hydroxyisobutyric Acid Amide and Methyl Formate 1.71 kg of $\alpha$-hydroxyisobutyric acid amide as obtained in the step (II), 3.0 kg of methyl formate, 2.0 kg of methanol and 27 g of powdery sodium methylate were placed in a 10-liter stainless-steel autoclave equipped with a stirrer, and reacted by heating with stirring at 60° C. for 2 hours.

The reaction product was cooled and then analyzed by gas chromatography. The result indicated that the conversion of $\alpha$-hydroxyisobutyric acid amide was 72.6%, the selectivity for methyl $\alpha$-hydroxyisobutyrate was 99.1% and the selectivity for formamide was 98.5%.

After neutralization of sodium methylate in the reaction solution with hydrochloric acid, the solution was distilled by the usual method to recover methyl formate, methanol and $\alpha$-hydroxyisobutyric acid amide, and at the same time, 1.39 kg of methyl $\alpha$-hydroxyisobutyrate having a purity of 99% or higher and 520 g of formamide having a purity of 99% or higher were obtained. The overall recovery rate including the recovery of intermediate distillate was quantitative.

Step (IV): Synthesis of $\alpha$-hydroxyisobutyric Acid by Hydrolysis of Methyl $\alpha$-hydroxyisobutyrate 1.22 kg of methyl $\alpha$-hydroxyisobutyrate obtained in the step (III), 540 g of water, and 50 g of strongly acidic ion exchange resin (Amberlite XH-105, produced by Rohm & Haas Co.) were fed to a 5-liter three-necked flask equipped with a distillate tube, a thermometer and a stirrer, and reacted at a reaction temperature of 95° C. for 4 hours while distilling out methanol with 95 weight % purity in a total amount of 340 g. The reaction solution was filtered at 90° C. to separate the ion exchange resin catalyst, and 1.38 kg of crude $\alpha$-hydroxyisobutyric acid was obtained. The result of gas chromatography pointed out that the conversion of methyl $\alpha$-hydroxyisobutyrate was 99.2%, and the selectivity for $\alpha$-hydroxyisobutyric acid was 99%.

Step (V): Synthesis of Methacrylic Acid by Dehydration of $\alpha$-hydroxyisobutyric Acid 100 g of crude $\alpha$-hydroxyisobutyric acid obtained in the step (IV), and 6 g of sodium hydroxide were fed to a 200 ml flask equipped with a stirrer. A McMahon packing layer (diameter: 20 mm, height: 300 mm) and a reflux condenser were fixed to the top of the flask. Another crude $\alpha$-hydroxyisobutyric acid was fed to the flask at a rate of 50 g/hr at a reaction temperature of 185° to 195° C. at 300 torr with heating and stirring. In order to prevent polymerization, p-methoxyphenol was dissolved in the feed liquid in a concentration of 0.4% by weight, and air was blown into the flask at the bottom thereof. The reaction was continued for 24 hours and 1.18 kg of reaction product was obtained. The compositions by weight of the reaction product were 60.8% methacrylic acid, 2.2% $\alpha$-hydroxyisobutyric acid and 36.4% water. The above compositions proved that the conversion of $\alpha$-hydroxyisobutyric acid was 97.1%, the yield of methacrylic acid was 96%, and the selectivity for methacrylic acid was 98.9%. It was possible to efficiently separate and recover highly pure methacrylic acid from the reaction product thus obtained by the usual method such as distillation, extraction or the like.

Step (VI): Production of Prussic Acid by Dehydration of Formamide 7.5 ml of spherical $\alpha$-alumina catalyst (calcined at 1500° C. for 2 hours) with a diameter of 2 mm was packed in a SUS 316 reactor with a inside diameter of 11 mm, and a small amount of air for dilution and formamide obtained in the step (III) were continuously fed under the conditions of 210 torr, 450° to 580° C. and the contact time of 0.03 second. The reaction was continued for 10 hours. Non-condensed gas was introduced into a gas washing bottle containing water so that the accompanying prussic acid was absorbed therein.

The condensed solution and the absorbing solution were analyzed. The result showed that the conversion of formamide was 99.4%, and the yield of prussic acid based on formamide was 94.0%.

Upon distillation of the product, there was obtained highly pure prussic acid, which was recycled as a starting material for the production of ACH.

EXAMPLE 2

As the step (III) of Example 1, 10.3 g of α-hydroxyisobutyric acid amide, 23.6 g of methanol and 0.2 g of powdery sodium methylate were placed in a 120 ml stainless-steel autoclave. In addition, carbon monoxide was introduced into the autoclave at a pressure of 40 atm with heating and stirring to effect reaction so that the reaction pressure was maintained at 40 atm when the temperature in the autoclave reached 60° C. After 3 hours of continuous reaction, the content in the autoclave was cooled to 10° C., the internal pressure was gradually lowered to the atmospheric pressure, and the product was taken out. The result of gas chromatographic analysis of the product indicated that the conversion of α-hydroxyisobutyric acid amide was 85.2%, the selectivity for methyl α-hydroxyisobutyrate based on α-hydroxyisobutyric acid amide was 98.8%, and the selectivity for formamide was 97.3%.

What is claimed is:

1. A process for producing methacrylic acid which comprises:
   (I) producing acetonecyanohydrin from prussic acid and acetone;
   (II) hydrating the acetonecyanohydrin obtained in the preceding step (I) to form α-hydroxyisobutyric acid amide;
   (III) reacting the α-hydroxyisobutyric acid amide obtained in the preceding step (II) with methyl formate to form methyl α-hydroxyisobutyrate and formamide;
   (IV) hydrolyzing the methyl α-hydroxyisobutyrate obtained in the preceding step (III) to form α-hydroxyisobutyric acid;
   (V) dehydrating the α-hydroxyisobutyric acid obtained in the preceding step (IV) to form methacrylic acid; and
   (VI) dehydrating the formamide separated from the products obtained in the above step (III) to form prussic acid and recycling the prussic acid to step (I) as a starting material.

2. The process as claimed in claim 1, wherein the reaction of prussic acid and acetone in the step (I) is carried out in the presence of a basic catalyst.

3. The process as claimed in claim 1, wherein the hydration of acetonecyanohydrin in the step (II) is carried out in the presence of manganese oxide catalyst. of acetonecyanohydrin in the step (II) is carried out in the presence of manganese oxide catalyst.

4. The process as claimed in claim 1, wherein the reaction of α-hydroxyisobutyric acid amide and methyl formate in the step (III) is carried out in a solvent and in the presence of a catalyst.

5. The process as claimed in claim 4, wherein the solvent is methanol.

6. The process as claimed in claim 4, wherein the catalyst is an alkali metal alcoholate or an alkaline earth metal oxide.

7. The process as claimed in claim 6, wherein the alkali metal alcoholate is sodium methylate, sodium ethylate, sodium butyrate, potassium methylate, potassium ethylate, or potassium butyrate.

8. The process as claimed in claim 6, wherein the alkaline earth metal oxide is magnesium oxide, calcium oxide, or barium oxide.

9. The process as claimed in claim 1, wherein the molar feed ratio of methyl formate to α-hydroxyisobutyric acid amide is from 1/1 to 10/1.

10. The process as claimed in claim 1, wherein the hydrolysis of methyl α-hydroxyisobutyrate in the step (IV) is carried out in the presence of a catalyst.

11. The process as claimed in claim 10, wherein the catalyst is a strongly acidic ion exchange resin.

12. The process as claimed in claim 1, wherein the dehydration of α-hydroxyisobutyric acid in the step (V) is carried out in the presence of a catalyst comprising an alkali metal hydroxide.

13. The process as claimed in claim 1, wherein the dehydration of α-hydroxyisobutyric acid in the step (V) is carried out in the presence of a polymerization inhibitor.

14. The process as claimed in claim 1, wherein the dehydration of formamide in the step (VI) is carried out under 10 torr to normal pressure at 350° to 600° C.

15. The process as claimed in claim 1, wherein the molar feed ratio of the methyl formate to the α-hydroxyisobutyric acid is from 2/1 to 5/1; the reaction of the prussic acid and the acetone in step (I) is carried out in the presence of a basic catalyst; the hydration of the acetonecyanohydrin in step (II) is carried out in the presence of a manganese oxide catalyst; the reaction of the α-hydroxyisobutyric acid amide and the methyl formate in step (III) is carried out at a temperature of 20° to 100° C. and for a time of 0.5 to 6 hours and in the presence of a catalyst selected from the group consisting of sodium methylate, sodium ethylate, sodium butyrate, potassium methylate, potassium ethylate, potassium butyrate, magnesium oxide, calcium oxide and barium oxide and the catalyst is in an amount of 0.001 to 0.30 moles per mole of the α-hydroxyisobutyric acid amide; the reaction of the α-hydroxyisobutyric acid amide and the methyl formate in step (III) is carried out in the presence of a methanol solvent; the molar feed ratio of the methanol to the α-hydroxyisobutyric acid amide is 2 to 10; the hydrolysis of the methyl α-hydroxyisobutyrate in step (IV) is carried out in the presence of a strongly acidic ion exchange resin catalyst; the dehydration of the α-hydroxyisobutyric acid in step (V) is carried out in the presence of a catalyst comprising an alkali metal hydroxide; the dehydration of the α-hydroxyisobutyric acid in step (V) is carried out in the presence of a polymerization inhibitor; and the dehydration of the formamide in the step (VI) is carried out at a pressure of 10 torr to normal pressure and at a temperature out 350° to 600° C.

16. A process for producing methacrylic acid which comprises:
   (I) producing acetonecyanohydrin from prussic acid and acetone;
   (II) hydrating the acetonecyanohydrin obtained in the preceding step (I) to form α-hydroxyisobutyric acid amide;
   (III) reacting the α-hydroxyisobutyric acid amide obtained in the preceding step (II) with methanol and carbon monoxide to form methyl α-hydroxyisobutyrate and formamide;
   (IV) hydrolyzing the methyl α-hydroxyisobutyrate obtained in the preceding step (III) to form α-hydroxyisobutyric acid;
   (V) dehydrating the α-hydroxyisobutyric acid obtained in the preceding step (IV) to form methacrylic acid; and (VI) dehydrating the formamide separated from the products obtained in the above step (III) to form prussic acid and recycling the prussic acid to step (I) as a starting material.

17. The process as claimed in claim 16, wherein the reaction of prussic acid and acetone in the step (I) is carried out in the presence of a basic catalyst.

18. The process as claimed in claim 16, wherein the hydration of acetonecyanohydrin in the step (II) is carried out in the presence of manganese oxide catalyst.

19. The process as claimed in claim 16, wherein the reaction of α-hydroxyisobutyric acid amide with methanol and carbon monoxide in the step (III) is carried out in a solvent and in the presence of a catalyst.

20. The process as claimed in claim 16, wherein the molar feed ratio of methanol to α-hydroxyisobutyric acid amide is from 1/1 to 30/1, and the carbon monoxide has a partial pressure from 10 to 500 kg/cm².

21. The process as claimed in claim 16, wherein the molar feed ratio of the methanol to the α-hydroxyisobutyric acid amide is from 1/1 to 30/1 and the carbon monoxide has a partial pressure of 20 to 300 kg/cm²; the reaction of the prussic acid and the acetone in step (I) is carried out in the pressure of a basic catalyst; the hydration of the acetonecyanohydrin in step (II) is carried out in the pressure of a manganese oxide catalyst; the hydration of the acetonecyanohydrin in the step (II) is carried out in the presence of manganese oxide catalyst; the reaction of the α-hydroxyisobutyric acid amide with the methanol and the carbon monoxide in the step (III) is carried out in the presence of a solvent and in the presence of a catalyst.

* * * * *